(12) United States Patent
Farrar et al.

(10) Patent No.: US 6,309,569 B1
(45) Date of Patent: Oct. 30, 2001

(54) ENCAPSULATION OF BIOACTIVE AGENTS

(75) Inventors: Graham Henry Farrar; Anne Margaret Tinsley-Bown, both of Salisbury (GB); David Hugh Jones, Montreal (CA)

(73) Assignee: Microbiological Research Authority, Salisbury (GB)

( * ) Notice: Subject to any disclaimer, the term of this patent is extended or adjusted under 35 U.S.C. 154(b) by 0 days.

(21) Appl. No.: 09/310,936

(22) Filed: May 13, 1999

(30) Foreign Application Priority Data

May 13, 1998 (GB) .................................................. 9810236

(51) Int. Cl.⁷ .............................. B01J 13/02; B01J 13/04; B01J 13/20; B05D 7/00
(52) U.S. Cl. ........................... 264/4.1; 264/4.3; 264/4.33; 264/4.6; 427/213.3; 427/213.31; 427/213.36
(58) Field of Search .......................... 264/4.1, 4.3, 4.33, 264/4.6; 427/213.3, 213.31, 213.36

(56) References Cited

U.S. PATENT DOCUMENTS

| | | | |
|---|---|---|---|
| 4,293,539 | 10/1981 | Ludwig et al. | 424/19 |
| 4,623,588 | 11/1986 | Nuwayser et al. | 428/402.24 |
| 4,652,441 | 3/1987 | Okada et al. | 424/19 |
| 4,711,782 | 12/1987 | Okada et al. | 424/455 |
| 4,741,872 | 5/1988 | De Luca et al. | 264/4.7 |
| 4,818,542 | 4/1989 | De Luca et al. | 424/491 |
| 4,853,226 | 8/1989 | Machida et al. | 424/426 |
| 4,897,268 | 1/1990 | Tice et al. | 424/422 |
| 4,917,893 | 4/1990 | Okada et al. | 424/423 |
| 4,933,105 | 6/1990 | Fong | 252/303 |
| 5,061,492 | 10/1991 | Okada et al. | 424/423 |
| 5,075,109 | 12/1991 | Tice et al. | 424/88 |
| 5,084,553 | 1/1992 | Hess et al. | 528/361 |
| 5,100,669 | 3/1992 | Hyon et al. | 424/426 |
| 5,160,745 | 11/1992 | De Luca et al. | 424/487 |
| 5,407,609 | 4/1995 | Tice et al. | 264/46 |
| 5,417,986 | 5/1995 | Reid et al. | 424/499 |
| 5,531,925 | 7/1996 | Landh et al. | 252/299.01 |
| 5,540,937 | 7/1996 | Billot et al. | 424/489 |
| 5,580,859 | 12/1996 | Felgner et al. | 514/44 |
| 5,589,466 | 12/1996 | Felgner et al. | 514/44 |
| 5,622,649 | 4/1997 | Hunter et al. | 252/309 |
| 5,639,473 | 6/1997 | Grinstaff et al. | 424/450 |
| 5,650,173 | 7/1997 | Ramstack et al. | 424/489 |
| 5,654,008 | 8/1997 | Herbert et al. | 424/489 |
| 5,656,469 | 8/1997 | Tresco et al. | 435/182 |
| 5,783,567 | 7/1998 | Hedley et al. | 514/44 |
| 5,814,344 | 9/1998 | Tice et al. | 424/501 |
| 5,820,883 | 10/1998 | Tice et al. | 424/501 |
| 5,869,103 * | 2/1999 | Yeh et al. | 424/501 |

FOREIGN PATENT DOCUMENTS

| | | |
|---|---|---|
| 2126685 | 5/1994 | (CA) . |
| 0 027 662 A1 | 4/1981 | (EP) . |
| 0 127 713 B1 | 12/1984 | (EP) . |
| 0 145 240 A2 | 6/1985 | (EP) . |
| 0 161 640 A2 | 11/1985 | (EP) . |
| 0 179 023 A2 | 4/1986 | (EP) . |
| 0 248 531 A2 | 12/1987 | (EP) . |
| 0 250 038 A2 | 12/1987 | (EP) . |
| 0 258 749 A2 | 3/1988 | (EP) . |
| 0 263 490 A2 | 4/1988 | (EP) . |
| 0 266 119 B1 | 5/1988 | (EP) . |
| 0 302 582 B1 | 8/1989 | (EP) . |
| 0 330 180 B1 | 8/1989 | (EP) . |
| 0 333 523 B1 | 9/1989 | (EP) . |
| 0 334 062 A2 | 9/1989 | (EP) . |
| 0 374 531 A2 | 6/1990 | (EP) . |
| 0 451 390 A1 | 10/1991 | (EP) . |
| 0 467 389 A2 | 1/1992 | (EP) . |
| 0 471 036 B1 | 2/1992 | (EP) . |
| 0 475 178 A1 | 3/1992 | (EP) . |
| 0 531 497 B1 | 3/1993 | (EP) . |
| 0 635 261 A1 | 1/1995 | (EP) . |
| 0 706 792 A1 | 4/1996 | (EP) . |
| 0 737 750 A2 | 10/1996 | (EP) . |
| 0 779 072 A1 | 6/1997 | (EP) . |
| 2185979 | 8/1987 | (GB) . |
| 2 234 896 | 2/1991 | (GB) . |
| 2 265 311 | 9/1993 | (GB) . |
| 2 310 801 | 9/1997 | (GB) . |
| WO 90/11092 | 10/1990 | (WO) . |
| WO 91/19487 | 12/1991 | (WO) . |
| WO 92/06666 | 4/1992 | (WO) . |
| WO 93/19183 | 9/1993 | (WO) . |
| WO 94/04171 | 3/1994 | (WO) . |
| WO 94/04260 | 3/1994 | (WO) . |
| WO 94/09898 | 5/1994 | (WO) . |
| WO 94/23699 | 10/1994 | (WO) . |
| WO 94/23738 | 10/1994 | (WO) . |
| WO 94/28873 | 12/1994 | (WO) . |
| WO 94/28874 | 12/1994 | (WO) . |
| WO 95/05853 | 3/1995 | (WO) . |
| WO 95/07072 | 3/1995 | (WO) . |
| WO 95/11009 A1 | 4/1995 | (WO) . |
| WO 95/17167 | 6/1995 | (WO) . |
| WO 95/20660 | 8/1995 | (WO) . |

(List continued on next page.)

OTHER PUBLICATIONS

Alexakis, T. et al., "Microencapsulation of DNA With Alginate Microsphere and Crosslinked Chitosan Membranes for In Vivo Application," *Appl. Biochem. Biotech.* 50:93–106 (1995).

(List continued on next page.)

Primary Examiner—Nathan M. Nutter
(74) Attorney, Agent, or Firm—Fish & Richardson P.C.

(57) ABSTRACT

Bioactive agent is encapsulated in a polymer microparticle in a (water-in-oil)-in-water emulsion-based method, and using a solvent that comprises ethyl acetate. Also described are microparticles comprising low inherent viscosity (i.v.) PLG, some with i.v. less than 0.5dl/g, and methods for their preparation. DNA release is modified through use of low i.v. PLG. A particle production method for scale-up uses a blender that avoids excessive shear damage to DNA being encapsulated.

15 Claims, 7 Drawing Sheets

FOREIGN PATENT DOCUMENTS

| | | |
|---|---|---|
| WO 95/21250 | 8/1995 | (WO) . |
| WO 95/24929 | 9/1995 | (WO) . |
| WO 95/31184 | 11/1995 | (WO) . |
| WO 95/31187 | 11/1995 | (WO) . |
| WO 95/35097 | 12/1995 | (WO) . |
| WO 96/00295 | 1/1996 | (WO) . |
| WO 96/11671 | 4/1996 | (WO) . |
| WO 96/29998 | 10/1996 | (WO) . |
| WO 97/35563 A2 | 10/1997 | (WO) . |
| WO 97/36578 | 10/1997 | (WO) . |

OTHER PUBLICATIONS

Truong, V.L. et al., "Immuno–microsphere as Gene Delivery Vehicle:Targeting of LAMP–1 to Lysosomal Membrane," *Proceed. Intern. Symp. Control. Rel. Bioact. Mater.* 21:142–143 (1994).

Truong–Le, V.L. et al., "Gene Transfer by Gelatin–DNA Coacervate," *Proceed. Intern. Symp. Control. Rel. Bioact. Mater.* 22:466–467 (1995).

Amagi, M. et al., "Autoanntibodies Against a Novel Epithelial Cadherin in Pemphigus Vulgaris, a Disease of Cell Adhesion," *Cell* 67:869–877 (1991).

Chen, S.C. et al., "Protective Immunity Induced by Oral Immunization with a Rotavirus DNA Vaccine Encapsulated in Microparticles," *J. Virol.* 72:5757–5761 (Jul. 1998).

Eldridge, J.H. et al., "Biodegradable and Biocompatible Poly(DL–Lactide–co–Glycolide) Microspheres as an Adjuvant for Staphylococcal Enterotoxin B Toxoid Which Enhances the Level of Toxin–neutralizing Antibodies," *Infect. Imm.* 59:2978–2986 (1991).

Eldridge, J.H. et al., "Controlled Vaccine Release in the Gut–Associated Lymphoid Tissues. I. Orally Administered Biodegradable Microspheres Target the Peyer's Patches," *J. Cont. Rel.* 11:205–214 (1990).

Florence, A.T. "The Oral Absorption of Micro– and Nanoparticulates: Neither Exception Nor Unusual," *Pharm. Res.* 14:259–266 (Mar. 1997).

Gref, R. et al., "Biodegradable Long–Circulating Polymeric Nanopheres," *Science* 263:1600–1603 (1994).

Heard, "HLA and autoimmune disease," in *HLA and Disease*, Academic Press, San Diego, CA, chapter 7 (1994).

Jacobs, S.C. et al., "High–Level Expression of the Tick--Borne Encephalitis Virus NS1 Protein by Using an Adenovirus–Based Vector: Protection Elicited in a Murine Model," *J. Virol.* 66:2086–2095 (1992).

Jepson, M. et al., "Comparison of Poly(DL–Lactide-c-o–Glycolide) and Polystyrene Microsphere Targeting to Intestinal M Cells," *J. Drug Targeting* 1:245–249 (1993).

Jeyanthi, R. et al., "Develpoment of a Biodegradable Microphere Formulation for the Sustained Release of a Bioactive Peptide," *Pharm. Res.* 8:151(S), pdd 7097 (1991).

Jones, D.H. et al., "Orally Administered Microencapsulated Bordetella pertussis Fimbriae Protect Mice from B. pertussis Respiratory Infection," *Infect. Immun.* 64:489–494 (Feb. 1996).

Jones, D.H. et al., "Poly(DL–lactide–co–glycolide)– encapsulated plasmid DNA elicits systemic and mucosal antibody responses to encoded protein after oral administration," *Vaccine* 15:814–817 (Jun. 1997).

Jones, D.H. et al., "Oral delivery of Poly(lactide–co–glycolide) encapsulated vaccines," *Behring Inst. Mitt.* 98:220–228 (Feb. 1997).

Jones, D.H. et al., "Immune Responses Following Oral and Parental Administration of Plasmid DNA Encapsulated in Poly(lactide–coglycolide) Microparticles," *Int. Meeting on Nucleic Acid Vaccines*, Bethesda, MD, Abstract and attached Figures 2 and 3 and Figure entitled Stool IgA Response to PLG–Encapsulated DNA (Feb. 5–7, 1996).

Jones, D.H. et al. "Oral Delivery of Micro–Encapsulated DNA Vaccines, " *Dev. Biol. Stand.* 92:149–155 (1998).

Jones, D.H. et al., "Protection of mice from Bordetella pertussis respiratory infection using microencapsulated pertussis fimbriae," *Vaccine* 13:675–681 (May 1995).

Jones, D.H. et al., "Poly(lactide–co–glycolide) microencapsulation of vaccine antigens," *J. Biotech.* 44:29–36 (1994).

Kreuter, J. "Nanoparticles and microparticles for drug and vaccine delivery," *J. Anat.* 189:503–505 (1996).

Murphy, D. et al. ,"A novel MHC class II epitope expressed in thymic medulla but not cortex," *Nature* 338:765–768 (1989).

Neutra, M. et al., "Epithelial M Cells: Gateways for Mucosal Infection and Immunization," *Cell* 86:345–348 (1996).

O'Hagan, D.T. " The intestinal uptake of particles and the implications for drug and antigen delivery," *J. Anat.* 189:477–482 (1996).

Puyal, C. et al., "A new cationic liposome encapsulating genetic material. A potential delivery system for polynucleotides," *Eur. J. Biochem.* 228:697–703 (1995).

Shimoda, S. et al., "HLA–DRB4 0101–restricted Immunodominant T Cell Autoepitope of Pyruvate Dehydrogenase Complex in Primary Biliary Cirrhosis: Evidence of Molecular Mimicry in Human Autoimmune Diseases," *J. Exp. Med* 181:1835–1845 (1995).

Steinman, L. "Escape from 'Horror Autotoxicus': Pathogenesis and Treatment of Autoimmune Disease," *Cell* 80:7–10 (1995).

Tomlinson, E. and Rolland, A.P. et al., "Controllable gene therapy Pharmaceutics of non–viral gene delivery systems," *J. Cont. Rel.* 39:357–372 (1996).

Visscher, G.E. "Biodegradation of and tissue reaction to 50:50 Poly(DL–lactide–co–glycolide) microcapsules," *J. Biomed. Mater. Res.* 19:349–365 (1985).

Dialog File 351, Accession No. 81–32924D/198119, Derwent WPI English language abstract for Document AL1 (EP 0 027 662 A1).

Dialog File 351, Accession No. 86–108252–198617, Derwent WPI English language abstract for Document AM1 (EP 0 179 023 A2).

Dialog File 351, Accession No. 92–166845/199220, Derwent WPI English language abstract for Document AL3 (WO 92/06666).

Dialog File 351, Accession No. 94–167187/199420, Derwent WPI English language abstract for Document AN3 (WO 94/09898).

Dialog File 351, Accession No. 95–123218/199516, Derwent WPI English language abstract for Document AM4 (WO 95/07072).

Dialog File 35, Accession No. 95–240449/199531, Derwent WPI English language abstract for Document AN4 (WO 95/17167).

European Patent Office, English language abstract for Japanese Patent No. 06–009377.

Crystal et al., "Transfer of Genes to Humans: Early Lessons and Obstacles to Success," *Science* 270:404–410 (1995).

Eppstein, D.A. and Longenecker, J.P., "Alternative Delivery Systems For Peptides and Proteins as Drugs," *CRC Crit. Rev. Ther. Drug Carr. Syst.* 5:99–139 (1988).

Etlinger, H. "Carrier sequence selection–one key to successful vaccines," *Imm. Today* 13:52–55 (1992).

Gunzburg, W.H. and Salmons, B., "Virus vector design in gene therapy," *Mol. Med. Today* 1:410–417 (1995).

Ledley, F. "Nonviral Gene Therapy: The Promise of Genes as Pharmaceutical Products," *Hum. Gen. Ther.* 6:1129–1114 (1995).

Marquet, P. et al., "Toxicity of Tungsten," *The Lancet* 349:58–59 (1997).

Miller, D.L. et al., "Comet Assay Reveals DNA Strand Breaks Induced by Ultrasonic Cavitation In Vitro," *Ultrasound Med. Biol.* 21:841–848 (1995).

Morris, W. et al., "Potential of polymer microencapsulation technology for vaccine innovation," *Vaccine* 12:5–11 (1994).

Nellore, R. et al., "Application of Biodegradable Microspheres to Hepatitus B Surface Antigen vaccination System," *Pharm. Res.* 8:151(S), PDD 7098 (1991).

Rajasubramanian, G. et al., "Fabrication of Resorbable Microporous Intravascular Stents for Gene Therapy Applications," *ASAIO J.* 40:M584–M588 (1994).

Sah, H.K. et al., "Biodegradable microcapsules prepared by a w/o/w technique: effects of shear force to make a primary w/o emulsion on their morphology and protein release," *J. Microencapsulation* 12:59–69 (1995).

Whalen, "DNA vaccines for emerging infectious diseases," *Emerging Infect. Dis.* 2:168–175 (1996).

* cited by examiner

ENCAPSULATION OF BIOACTIVE AGENTS

FIELD OF THE INVENTION

The present invention relates to improvements in encapsulation of bioactive gents, such as antigens, drugs and DNA for vaccination and gene therapy. In articular, the present invention relates to methods for encapsulating antigen and/or DNA, in aqueous solution, in a polymer microparticle, so that the microparticles when administered to a recipient deliver antigen to antigen presenting cells of the recipient, and/or induce expression of the DNA in the recipient in the antigen presenting cells. The present invention relates also to microparticles and compositions comprising microparticles.

BACKGROUND OF THE INVENTION

The present technology of microencapsulation is currently at least 10 years old but does not seem to have yielded any commercially successful products, despite many announced breakthroughs. Indeed, apart from WO-A-97117063 (by the same inventors as the present invention), published methods have been found to be inefficient and unreliable.

Many published patents and applications are in the name of the Southern Research Institute (SRI). In particular, U.S. Pat. No. 5,407,609 purports to describe in example 7, an emulsion based method for the manufacture of hollow particles. Another emulsion based method for making particles that contain a protein, specifically BSA, is described in Sah et al (J Microencapsulation, 1995, vol. 12, No. 1, pp 59–69). If these particles are to be used as a means of administering an encapsulated bioactive agent to antigen-presenting cells in the gut epithelium, it is of great importance that their size be below 10 microns in diameter. Larger particles are not endocytosed by the targeted gut cells and pass through the gut without effect.

However, the methods detailed in U.S. Pat. No. 5,407,609 and by Sah et al succeed in making relatively large particles, or at least particles over a wide range of sizes, where a significant portion of particles are larger than the biological activity cut off point of 10 microns. A large spread of particle sizes, such as that seen in U.S. Pat. No. 5,407,609 inevitably leads to much of the encapsulated agent being incorporated in particles of a size that are not appropriate for phagocytosis. Worse still, Sah et al obtained a mixture of particle sizes with an apparent minimum diameter of around 10 microns. Both art methods are, therefore, not specifically designed to produce encapsulated product available for uptake by antigen-presenting cells. The encapsulation method used by Sah also requires very high shear rates during encapsulation, shear rates that would have a detrimental effect upon, and are thus unsuitable for, encapsulation of agents such as DNA.

U.S. Pat. No. 5,407,609 makes reference to the construction of microbubble-like particles but emphasises that water soluble agents are not easily encapsulated in such particles due to a tendency for the encapsulated agent to migrate out of that part of the emulsion that will eventually constitute the internal content of the particles. To overcome this problem, U.S. Pat. No. 5,407,609 requires that as soon as the emulsion has formed it be immediately added to a large volume of extraction medium i.e. water. However, in doing so control over particle size may be lost.

The internal architecture of microparticles made using the Sah method is generally a honeycombed matrix, illustrated in the photographs that accompany the Sah paper, rather than a simple, hollow microbubble-like structure. Incomplete removal of solvent and/or water from the insides of these matrices during the solvent extraction step and subsequent lyophilisation can result in the premature degradation of the polymer of the particle and a corresponding fall in the pH of any encapsulated aqueous solution, leading to damage of an encapsulated agent.

The bioactive agent release profile of administered microparticles has been previously altered by changing the relative amounts of lactide and glycolide present in PLG polymer. Much of this data is however based on "microsphere" technology where the encapsulated agent is distributed throughout a polymer matrix and there is no known prior art that relates to control of the release profile of microbubble particles. Altering the relative amounts of lactide and glycolide present in the PLG polymer has shown limited success in the short term but it would be desirable to provide alternative means of controlling the release profile.

WO-A-97/17063 describes methods for obtaining significant levels of incorporation of DNA into microparticles however, the authors of the present invention would like to improve upon this incorporation efficiency.

The present invention thus seeks to overcome, or at least ameliorate, the problems observed in the art. in particular, preferred embodiments of the invention aim to provide improved technology for the encapsulation of bioactive agents such as antigen and/or nucleic acids in polymer microparticles for the delivery of antigen and/or gene based prophylactics and therapies.

SUMMARY OF THE INVENTION

Accordingly, the present invention provides a method of encapsulating DNA in a polymer microparticle, comprising:

dissolving polymer in a solvent to form a polymer solution;

preparing an aqueous solution of DNA;

combining the polymer and DNA solutions with agitation to form a water-in-oil emulsion;

adding the water-in-oil emulsion to a further aqueous phase containing a stabiliser or surfactant with agitation to form a (water-in-oil)-in-water emulsion;

adding the (water-in-oil)-in-water emulsion to excess of an aqueous phase to extract the solvent, thereby forming polymer microparticles of a size up to 10 microns in diameter, said microparticles containing DNA;

wherein the DNA comprises a coding sequence and induces expression of the coding sequence in a recipient following administration, and wherein the solvent comprises ethyl acetate.

Figure 1:
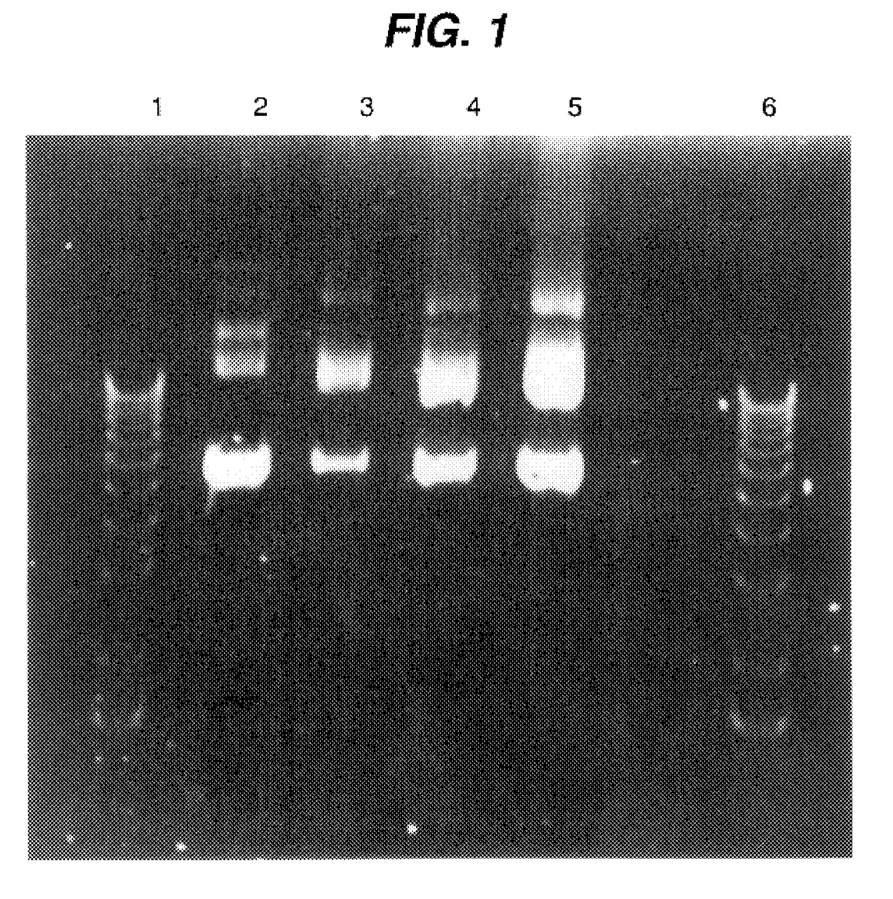
FIG. 1 is an agarose gel that shows the physical state of the DNA recovered from microparticles prepared with dichloromethane (prior art solvent) and ethyl acetate (in accordance with the invention)

In particular, FIG. 1 shows an agarose gel showing the relative amounts and the relative physical state of DNA recovered from equivalent weights of PLG microparticles prepared using either dichloromethane (prior art:Lane 3) or ethyl acetate (in accordance with the invention:Lanes 4 (high mol.wt. PLG), Lane 5 (low mol. wt. PLG)). Lane 2 is the control DNA (stock) showing a large proportion of super-coiled from (lower band) and Lane 1 &6 are the molecular weight markers. Comparison of Lane 3 with Lanes 4&5 suggests that ethyl acetate not only promotes the encapsulation of DNA, but also results in the retention of a greater proportion of the super-coiled form (lower band) compared with open circle form (upper band). It should be noted that the lower incorporation of DNA in the preparation analyzed in Lane 4 (high mol. wt. PLG) is a result of microparticle formation in the presence of limiting polymer due to its lower solubility in ethyl acetate.

Figure 2:
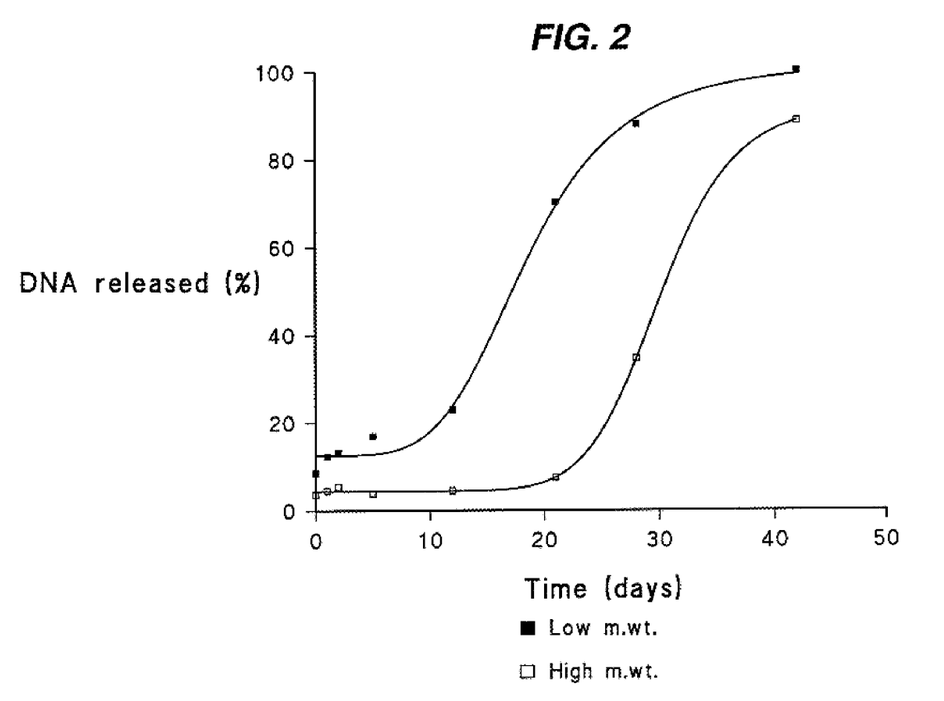
FIG. 2 shows release profiles of DNA from PLG microparticles prepared from high or low molecular weight polymer.

FIG. 2 shows the in vitro release kinetics of the PLG microparticles, of the invention. Microparticles were prepared using high (■-■), or low (◊-◊) molecular weight PLG. DNA concentrations in aliquots of supernatants serviced from sterile incubations of microparticle suspended in buffer maintained at 37 degrees C, were measured using optical absorption spectroscopy.

Figure 3A:
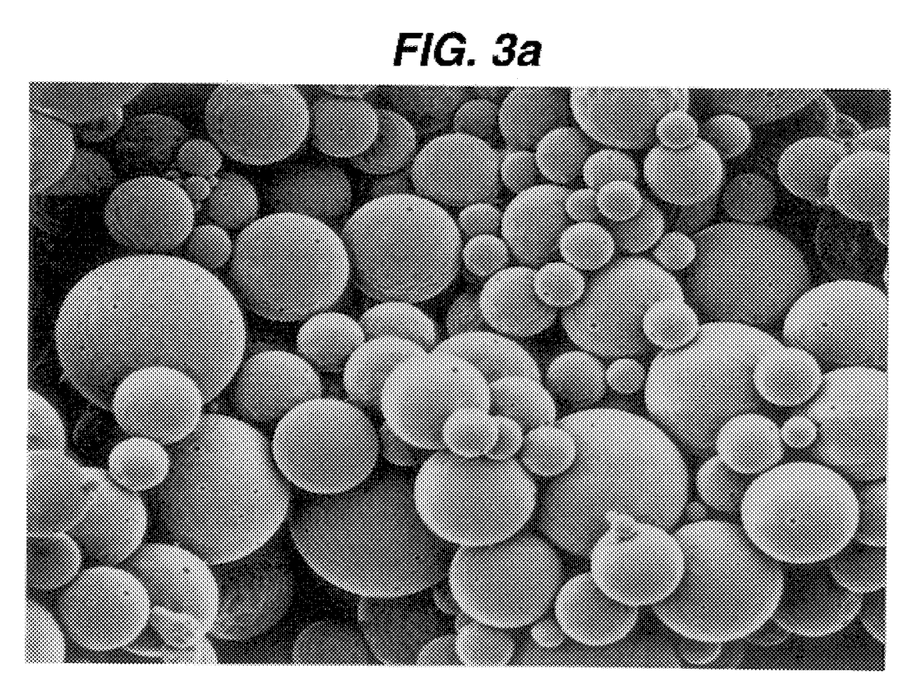
FIGS. 3a, 3b, 4a and 4b show scanning electron micrographs of prior art and inventive microparticles.

FIG. 3a shows a preparation of PLG microparticles (prepared according to the present invention) that have been applied to an EM specimen grid as a lyophilised powder. The uniformity of spherical structure indicates that the particles are not adversely effected by freeze-drying.

Figure 3B:
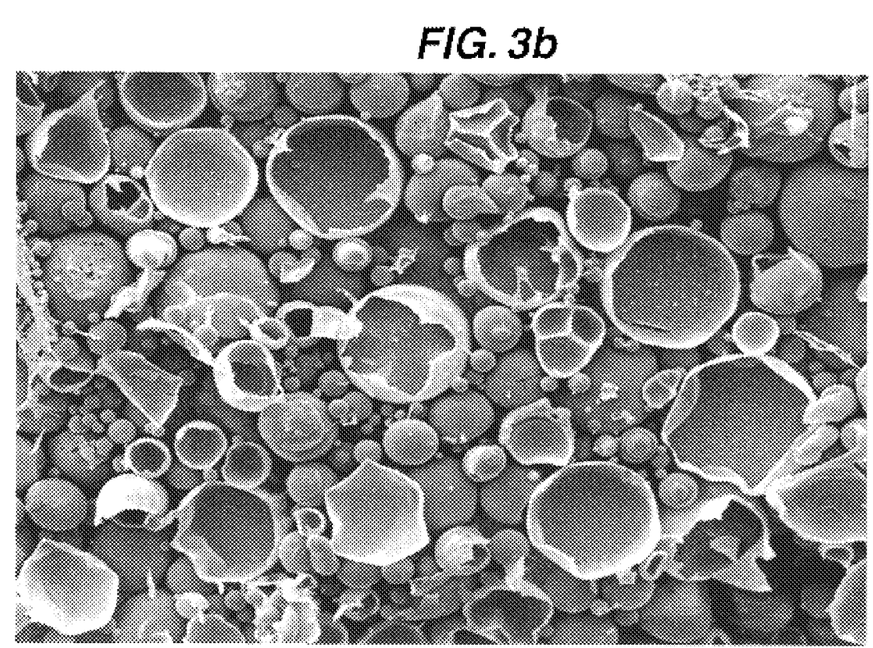

FIG. 3b demonstrates the "shell-like" structure of PLG microparticles (according to the present invention) prepared under optimal conditions. The specimen was freeze fractured. The hollow interiors of these particles can be clearly seen and are very different from examples given in the prior art.

Figure 4A:
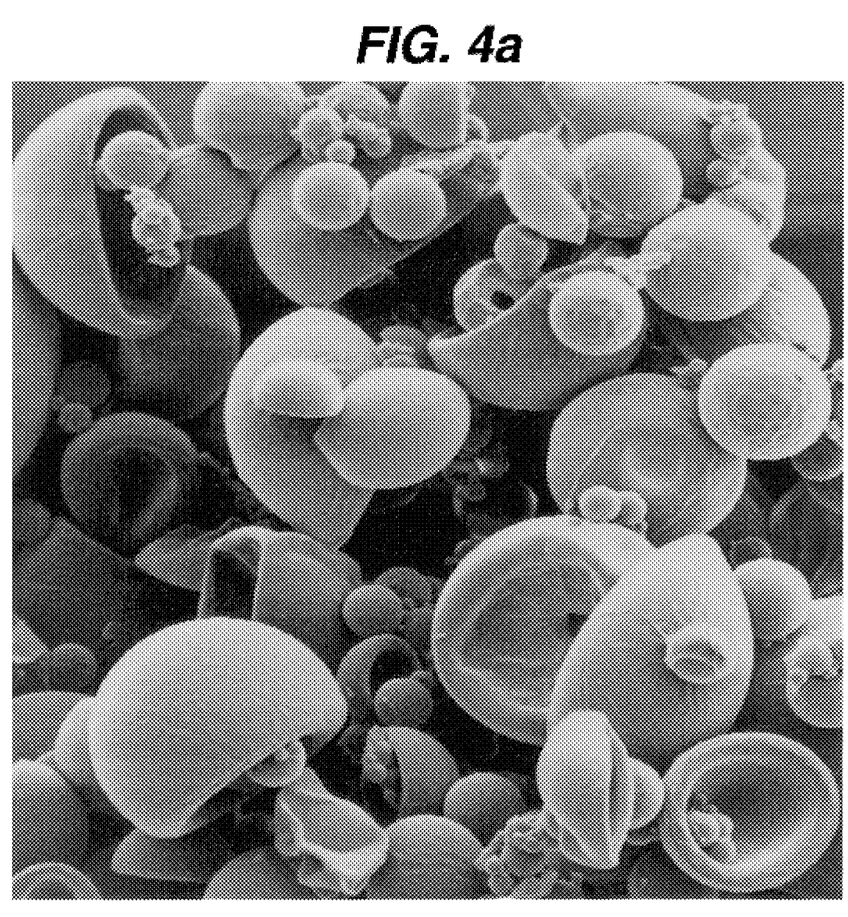

FIG. 4a shows a preparation of PLG microparticles (prepared according to the present invention), that have been dried from a hydrated slurry onto EM specimen grid at room temperature. The stresses encountered as the water evaporated have induced structural collapse to differing extents, indicating that the microparticles may comprise a "shell-like" structure with a hollow interior.

Figure 4B:
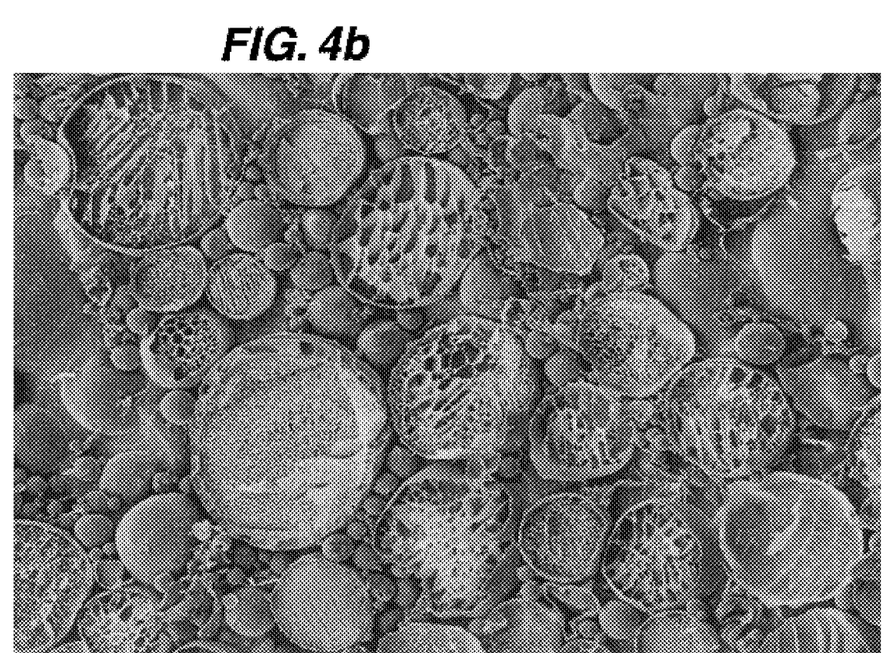

FIG. 4b shows the internal structure of microparticles prepared under conditions of excess (greater than 4:1) solvent: aqueous ratio. Preparations were frozen using liquid nitrogen and specimens were fractured whilst frozen to reveal particles with different elaborate internal structures.

Figure 5:
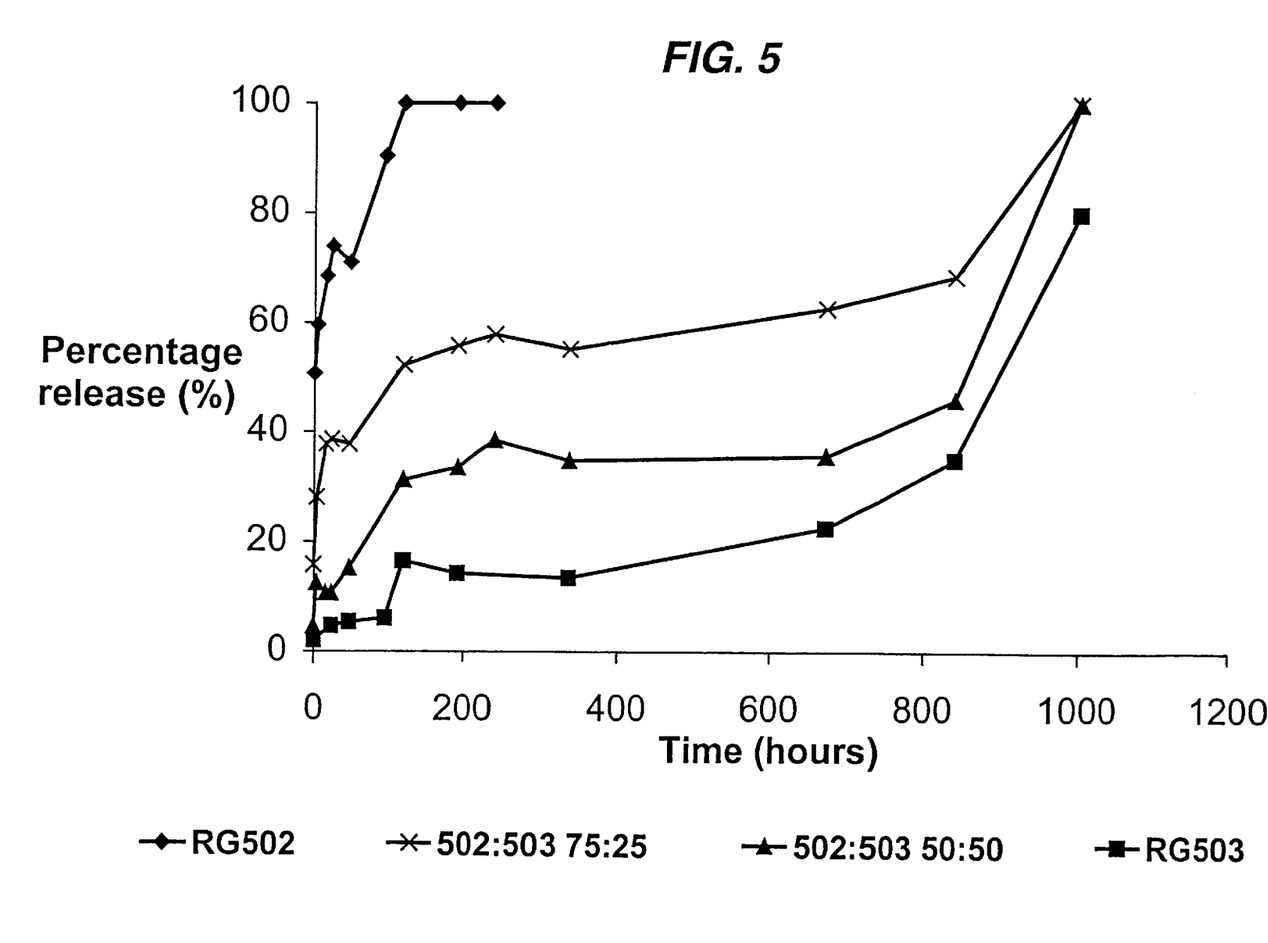
FIG. 5 shows DNA release profiles of preparations of microparticles made from PLG of different inherent viscosities.

FIG. 5 shows the percentage of DNA released over time from PLG microparticles made from PLG preparations of varying inherent viscosities. Low inherent viscosity PLG is denoted RG502 and higher inherent viscosity PLG is denoted RG503. DNA release from microparticles made from mixtures of 50:50 and 75:25 of RG502 and RG503 are also shown and represent PLG preparations of inherent viscosity in between those of RG502 and RG503.

DESCRIPTION OF THE PREFERRED EMBODIMENTS

Following the methods of the invention it is advantageously found that preparations of microparticles are obtainable with DNA being encapsulated in such a way that it retains its ability to induce expression of its coding sequence—as confirmed by transformation and transfection assays using DNA recovered from microparticles. The preparations are suitable for inducing protective immunity in a recipient after oral administration of the DNA coding for an appropriate antigen. The sizes of microparticles are generally less than 10 microns in diameter, thus increasing the proportion of agent available to antigen presenting cells. (Eldridge J. H. et al, J. Controlled Release, Volume 11, 1990, pages 205–214). Also, the efficiency of incorporation of DNA into the microparticles is improved and in preferred embodiments of the invention has been found to approach 80%, this latter figure representing a significant advance over the art.

The method of the invention is thus essentially a solvent extraction method, in which extraction of solvent after the second emulsion stage, i.e. after forming the (water-in-oil)-in-water emulsion, solidifies or consolidates the polymer of the microparticles. Reference to "forming polymer microparticles" is intended as a reference to the overall method in which microparticles are initially formed via an emulsion and polymer shells of the microparticles are then solidified or consolidated by solvent extraction.

The solvent used to dissolve the polymer can be extracted from the (water-in-oil)-in-water emulsion in a number of ways. In a specific example of the method of the invention described below, the (water-in-oil)-in-water emulsion is quenched in a large volume (100 ml-1 l) of warm water (37 degrees celsius is used in the example), thereby facilitating evaporation of the solvent from the polymer into the water. Other examples of solvent extraction are known, and include use of larger volumes of water at room temperature and use of a rotary evaporator.

One method of determining the incorporation efficiency of the method of the invention is to accurately measure, by optical absorption spectroscopy, the amount of DNA that is released from known weights of microparticles and relating this quantity to the original amount of DNA used. Using this method of optical measurement, it is observed that, in preferred embodiment of the invention, incorporation efficiency typically of 60–70% is achieved, representing a significant advance over the prior art methods.

The DNA contained within the microparticle will typically comprise double stranded DNA. The construction of a suitable DNA sequence for use in the invention will be appreciated by persons of skill in the art and is described in WO-A-97/17063. It is preferred that the sequence comprises both a transcriptional promoter and a gene coding sequence. It is further preferred that the DNA sequence provides for transcription termination and polyadenylation downstream of the coding sequence.

It is particularly preferred that the DNA be double stranded, circular and super coiled. It has been observed that during manufacture of microparticles the DNA is subjected to shear forces. Using the particle manufacturing conditions of the invention, the inventors have managed to retain significant amounts of functional DNA, though have observed that previously supercoiled DNA may become partly converted to the open circular form during the process. The degree to which the encapsulation process denatures DNA can be assessed by separating the native (supercoiled) DNA from partially denatured (open circle) and denatured (nicked and degraded) DNA, using agarose gel electrophoresis. A typical example of such a separation is illustrated in FIG. 1 where clearly defined bands correspond to the two most abundant form of DNA in the preparations—super-coiled (lower band) and open circular (upper band). Total degradation of the DNA is usually interpreted from a disappearance of bands corresponding to the two common forms.

The retention of biological activity of the encapsulated DNA, a measure of the retention of the preferred physical state, can be assessed, following release of DNA from the microparticle, by measuring the capacity of known amounts of DNA to either transform competent bacteria or transfect eukaryotic cells in culture. The transformation assay measures the introduction of a functional antibiotic resistance gene (e.g. β-lactamase) which is present in the plasmid and which confers ampicillin resistance to susceptible bacteria. Expression of this gene indicates the overall retention of DNA structure. The transfection assay specifically measures the functionality of the plasmid to induce expression of the gene of interest in suitably manipulated cells in culture. In both cases the indexes of activity obtained are compared to the activity of equivalent amounts of corresponding stock DNA.

Plasmid DNA or DNA derived therefrom by conventional manipulations is particularly suitable. As there is extensive literature relating to plasmid manufacture a person of skill in the art will readily be able to prepared a plasmid suitable for the microparticle of the invention. In general, plasmids incorporating any eukaryotic or prokaryotic promoter sequence are suitable.

The polymers most suitable for preparing the microparticles of the invention typically exhibit a number of properties. Such polymers should be of low toxicity, ideally pharmaceutically acceptable and soluble in the solvent adopted, such as in ethyl acetate either with or without a cosolvent, preferably to a level of at least around 50 mg/ml. In addition, they are typically biocompatible and biodegradable although it is preferable that they be sufficiently stable to pass through the acid conditions of the stomach. Nevertheless, the invention is not intended in its broadest aspects to be limited to a particular single polymer. Polymers based on poly (amino acids/derivatives of amino acids) are suitable and some specific examples of these are polymers including poly(lactide), poly(glycolide) and/or poly (lactide—co-glycolide). In a specific embodiment of the invention, described in more detail below, the polymer is poly-(DL lactide—co-glycolide) (PLG), and the concentration of PLG in the polymer solution is typically at least 10% wt/volume. In another specific embodiment of the invention also described below, the polymer is polycaprolactone.

The ratio of lactide to glycolide in the PLG suitable for manufacturing the microparticles of the invention is not critical and commercially available polymers include lactide:glycolide ratios of 25:75, 50:50 and 75:25 though the ratio can suitably be anywhere in the range 0:100 to 100:0. In particularly preferred embodiments of the invention the polymer is PLG of a molecular weight greater than 70kD, or less than 50kD. Other suitable polymer formulations for microparticles according to the present invention include poly—hydroxybutyrate, poly hydroxyvalerate, poly (hydroxybutrate/valerate), ethyl cellulose, dextran, polysaccharides, polyalkylcyanoacrylate, poly-methylmethacrylate, poly(e-caprolactone), polyhydrazines and mixtures of all of these components.

A further aspect of the invention relates to the universality of the method used to prepare the microparticles. Specifically, the inventors have made microparticles using polymers across a wide range of molecular weights without substantial modification of the basic methodology. Accordingly, the invention provides a method of encapsulating a bioactive agent in a polymer microparticle, comprising:

dissolving polymer in a solvent to form a polymer solution;

preparing an aqueous solution of the bioactive agent;

combining the polymer and bioactive agent solutions with agitation to form a water-in-oil emulsion;

adding the water-in-oil emulsion to a further aqueous phase containing a stabiliser or surfactant with agitation to form a (water-in-oil)-in-water emulsion;

adding the (water-in-oil)-in-water emulsion to excess of an aqueous phase to extract the solvent, thereby forming polymer microparticles of a size up to 10 microns in diameter, said microparticles containing the bioactive agent; wherein the polymer comprises or consists of PLG of molecular weight of 40kD or lower.

Preferably, the molecular weight of the PLG is 30kD or lower, and in specific embodiments of the invention microparticles comprise PLG of 3kD, 6kD, 9kD, 22kD and mixtures thereof. The molecular weight range of suitable polymer is 1.5kD –250kD. We have used commercial preparations of 3, 6, 9, 12, 18, 22, 60, 65 & 90kD. Hydrolysis rate of the polymer is related to the molecular weight and thus the lower molecular weight polymers will degrade more quickly.

When microparticles are honey-combed in structure, as has been proposed in Sah et al, the aqueous phases in the polymer matrix will not be lyophilised during freeze drying. This could explain the frequently observed denaturation of the biological agent and decreasing pH of the prior art preparations as the wet polymer hydrolysed to glycolic and lactic acids. We have observed that microparticles made according to the present invention collapse if treated harshly suggesting they have empty interiors from which water has been removed.

The microparticles of the present invention are in fact shell like, (FIG. 3b) and not solid, honey-combed or enclosing a material phase of any sort other than water when hydrated. Further, the microparticles of the present invention can be dried, for example by freeze drying without loss of the spherical structure (FIG. 4a). The present invention thus enables preparation of microparticles containing dry PDNA which will be far more stable than aqueous preparations.

Manufacture of the microparticles of the invention enables incorporation into the microparticles of any water-soluble substances, even any water-dispersible substances, though preferably the bioactive agent is selected from RNA, protein antigen, non-protein antigen, protein-or peptide-conjugated polysacharrides, protein-or peptide-DNA complexes, synthetic peptides, synthetic proteins, DNA viruses, cytokines, cancer therapeutics, mini-genes and water-soluble pharmaceuticals. The bioactive agent may further be accompanied by excipient and/or adjuvant, one example of which is alum.

Virtually any recombinant or native protein antigen may be encapsulated using the methods of the present invention, in particular any recombinant or native antigen useful to immunise against any pathogenic organism. By way of example only, a protein antigen for incorporation into microparticles of the present invention is optionally selected from:

(a) the antigens FHA, PT, 69kD-Pertactin, tetanus toxin, gp48, NS1, Capsid, gp350, NS3, SA, I, NP E, M, gp340, F, H, HN, 35kD protein, BP1, E1, E2, C, M, E and MSHA according to table 4;and (b) immunogenic fragments, variants and derivatives of the polypeptides of (a).

Details of Accession numbers of gene sequences for these antigens are listed in table 4.

In a (water-in-oil)-in-water emulsion system of the present invention the water droplet containing the DNA or bioactive agent is dispersed within the oil which is itself dispersed within the second water phase. This might result in the formation of 'currant buns' the currants being the aqueous phase+ DNA and the bun the polymer. In the present invention, the generation of this initial water-in-oil emulsion and its dispersion into the second water phase play a major part in the formation and character of the final microparticle. The generation of our microparticles is heavily influenced by the initial emulsification stage as the resultant microparticles correspond to individual droplets from the dispersed DNA- or bioactive agent-containing aqueous phase. It is around these that polymer has condensed. In preferred embodiments of the invention, the concentration of the polymer and the ratio of polymer solution to the initial aqueous phase are controlled to influence the microparticles obtained.

Specifically, in preferred embodiments of the invention the ratio of solvent:aqueous phase in formation of the water-in-oil emulsion is in the range of 4:1 to 20:1 (volume:volume), more preferably 5:1 to 15:1 and even more preferably 5:1 to 12:1 (volume:volume). Selection of ratios within these ranges dictates the formation of an initial water-in-oil emulsion that is instrumental to determining the size range and architecture of the resultant microparticles, and improves the efficiency of incorporation of DNA into the microparticles. When the ratio of solvent:aqueous phase falls below about 4:1, there is a significant reduction in the incorporation of bioactive agent, such as DNA, into the microparticles. This is the result when insufficient polymer containing phase is available to effectively coat the aqueous droplets thus preventing shell formation and loss of bioactive agent into the aqueous environment of the second emulsion phase. The incorporation efficiency increases with a ratio of at least 4:1 and preferably at least 5:1. When the ratio goes beyond about 20:1, then it becomes extremely difficult to prevent formation of "currant bun"-type structures as shown in the Sah paper. This is a consequence of an excess of polymer containing phase, which percents the dissociation of individual shell structures resulting in conglomerations into "currant bun" structure and solid microparticles showing polymer matrix inside. The structures are many times larger than 10 microns in diameter and thoroughly unsuitable for oral immunisation according to the invention. Below about 20:1 and preferably below about 15:1, the propensity for the method to produce these "currant bun"-type structures falls and microparticles of up to 10 microns in diameter are more readily formed.

Solvents suitable for use in dissolving the polymer are preferably of low toxicity and are ideally selected from the category lll list of solvents approved for pharmaceutical use. Solvents in the category ll list can also be used, though for human use it will usually be necessary to determine the amount of residual solvent in the particles before such particles can be pharmaceutically approved. Such solvents will dissolve preferably at least around 50 mg/ml of polymer and should be substantially immiscible with water, thereby facilitating the formation of a (water-in-oil)-in-water emulsion. In preferred embodiments of the invention the solvent exhibits a high vapour pressure so that the final solvent extraction step can be carried out quickly. Examples of solvents suitable for use in the method of the invention include ethyl acetate, dichloromethane, chloroform, propylene carbonate, and mixtures thereof. Acetone can also be used in solvent mixtures, ie as a cosolvent, but not on its own as it is miscible with water.

It is further preferred that the solvent comprises ethyl acetate either with or without a co-solvent which increases the amount of polymer that can be dissolved in the solvent. A number of co-solvent combinations are suitable, provided that the major proportion of the mixture is ethyl acetate (or another pharmaceutically accepted solvent). The advantages for employing co-solvent systems are twofold. First, the solvent combinations dissolve a greater weight of polymer than in single component solvents, which is advantageous when attempting to reduce the ratio of solvent aqueous phase in generation of the initial emulsion. Second, the co-solvents facilitate the dissolution of high molecular weight polymers, allowing the maintenance of critical solvent aqueous phase ratios with the less soluble polymers. Examples of such co-solvents include propylene carbonate and acetone. More generally, the invention also provides use of a co-solvent in combination with any suitable solvent for reparation of a polymer solution for use in preparation of a microparticle, and the methods of the invention are thus not limited to solvents which necessarily comprise ethyl acetate. For example, a solvent being a combination of dichloromethane and acetone, dissolving a greater weight of polymer than is dissolved by dichloromethane on its own, is another aspect of the invention. Further aspects of the invention include the use of any pharmaceutically solvent in combination with a co-solvent such as acetone whereby the combined solvent dissolves a greater weight of polymer than the pharmaceutically acceptable solvent on its own.

It is also preferred especially when DNA is being encapsulated that the emulsification steps of the method be carried out under conditions of reduced shear stress, and this is optionally achieved by use of an emulsifying energy, such as speed in the case of an emulsifying mixer, that is sufficient to obtain an emulsion and to form microparticles in the desired size range but not so high that all DNA is damaged by excessive shear. In an embodiment of the invention, described below, the emulsifying mixer speed is modified so that at least 25% of the DNA biological activity (assayed by transformation of competent bacteria or transfection of cultured cells) is retained in the resultant microparticles that contain DNA. Suitable mixer speeds in the case of a Silverson mixer are below 8000 rpm, preferably below 6000 rpm, and in specific embodiments described below the speeds are about 3000 rpm or above about 2000 rpm. Every variation of equipment that can be used to generate the emulsion phases will require assessing at different speeds and under different conditions. It is left for those skilled in the art to identify optimal speeds and duration of emulsification for each piece of apparatus. Using the Silverson Homogeniser at speed above 8000 rpm, there is significant damage to DNA and below about 2000 rpm there is very little or no formation of microparticles of size 10 microns or less in diameter. A more detailed analysis of the effect of mixer speed using a Silverson mixer is found in WO-A-97/17063.

The steps preliminary to and during formation of microparticles are thus adapted to input sufficient energy so as to form microparticles in the desired size range, which is typically 0.01–10 microns, but not so much energy that DNA or bioactive agent is damaged during the process. There is a balance required as more vigorous agitation such as through higher mixer speeds typically results in smaller microparticle sizes. But, DNA may be damaged by excessive agitation during emulsification. On the other hand, reducing the energy input during emulsion formation may have the effect that no emulsion is formed and no microparticles can be obtained. The invention enables a balance of these competing factors, to provide for formation of microparticles retaining an acceptable degree of biological activity.

In further embodiments of the invention, the method comprises maintaining the emulsification of the polymer and aqueous solutions to form the initial water-in-oil emulsion over a prolonged period of time, so as to obtain aqueous phase droplets a high proportion of which will result in microparticles of a size up to 10 microns in diameter. This has the advantage that with prolonged agitation during formation of the water-in-oil emulsion the size distribution of the microparticles becomes more homogenous.

Longer emulsification reduces the proportion of microparticles that are bigger than 10 microns. In addition, prolonged emulsification at different emulsification energies produces size distributions centred around different points—higher energies producing smaller average microparticle sizes. Hence, the method can be modified so as to tailor the obtained sizes to the size desired. Some prior art has suggested in connection with uptake of microparticles through the Peyer's patches that microparticles of 1 to 5 microns and those of 5 to 10 microns are taken up differently, and the present invention facilitates manufacture of microparticles with any chosen average diameter. It is also preferred to maintain the agitation of the polymer and aqueous solutions to form the water-in-oil emulsion over a prolonged period of time so as to obtain microparticles the majority of which and preferably substantially all of which are of a size up to 10 microns in diameter and more than 0.1 microns in diameter. In this context, reference to substantially all particles is intended to indicate that at least three quarters of the particles by number, and preferably at least 90%, are of size within the chosen diameters.

It is also a preferred to intercalate rest pauses between emusion cycles so as to allow any heat build up that occurs during agitation of the emulsion to dissipate and thereby reduce damage to the bioactive agent being encapsulated.

In particular embodiments of the invention, described below in further detail, there is provided a method for encapsulating a bioactive agent in a polymer microparticle, comprising:

- dissolving the polymer in a solvent to form a polymer solution;
- preparing an aqueous solution of a bioactive agent;
- combining the polymer and aqueous solutions with agitation to form a water-in-oil emulsion;
- adding the water-in-oil emulsion to a further aqueous phase with agitation to form a (water-in-oil)-in-water emulsion;
- adding the (water-in-oil)-in-water emulsion to excess of an aqueous phase to extract the solvent, thereby forming polymer microparticles of a size up to 10 microns in diameter;
- wherein agitation of the polymer and aqueous solutions, and agitation of the water-in-oil emulsion and the further aqueous phase, are carried in a blender.

The invention further provides for a method of preparing bioactive agent encapsulated within polymer microparticles of the invention using a blending apparatus for performing the emulsion steps. The blending apparatus comprises:

- a container for a liquid to be mixed;
- a blade for mixing liquid in the container;
- wherein the blade rotates about an axis of rotation and exerts a mixing action that includes driving liquid in a direction substantially along the axis of rotation.

The rotational action of the blade imparts emulsion energy into the liquid by establishing a rapidly circulating vortex within the liquid of the chamber. Thus the action of the apparatus is distinguished from other mixers which employ spinning probes that draw up liquid which is then extruded through an emulsor screen. Such an action produces significant shear forces and is highly damaging to DNA. An advantage of the present apparatus is that the bioactive agent such as DNA is subjected to lower shear and other stresses during encapsulation. The blending action of the apparatus is also distinguished from sonication mixers which employ ultrasound pulses to impart emulsion energy in to the liquid. Ultrasound is also damaging to DNA and can cause fragmentation of polynucleotide strands.

The emulsion steps are preferably carried out using apparatus which is a blender/mixer of the Waring (RTM) type. Thus the blender comprises a chamber for blending and mixing the emulsion, and further comprises a rotatable blade fixably mounted within said chamber, which blade includes a plurality of blade end tips extending upwardly and/or downwardly from the blade and may be roughly at 30–60 degrees to the blade or even perpendicular to the blade and thus parallel to the axis of rotation.

It is an advantage of use of the apparatus according to the invention that this method is appropriate for scale-up to industrial production of microparticles, in sharp contrast to the use of a homogeniser which would be appropriate only for tiny volumes of liquids suitable for experimental purposes.

The present invention also relates to modification of the polymer shell to achieve modified release rates of the particle contents.

Accordingly, the present invention provides a composition comprising microparticles of less than 10 microns in diameter which contain an external polymer shell and an internal aqueous solution of a bioactive agent, said composition comprising a microparticle wherein the polymer is PLG of molecular weight less than 50 kD, and preferably down to 1.5 kD.

The present invention additionally provides a composition comprising microparticles of less than 10 microns in diameter which contain an external polymer shell and an internal aqueous solution of a bioactive agent, said composition comprising a microparticle wherein the polymer is PLG of molecular weight more than 70 kD, and preferably up to 250 kD.

The present invention still further provides a composition comprising mixtures of microparticles of less than 10 microns in diameter which contain an external polymer shell and an internal aqueous solution of a bioactive agent, said composition comprising a first microparticle wherein the polymer is PLG of molecular weight less than 50 kD and a second microparticle wherein the polymer is PLG of molecular weight more than 70 kD. Very complex mixtures of individual types of polymer particles can be mixed and used as combination vaccines or therapies.

Where possible, however, the molecular mass distributions of the polymers suitable for use in the invention are quoted in terms of their inherent viscosities (i.v.). The i.v. is a quantifiable value that is easily measured and is known to be correlated to molecular mass distribution. It is therefore often a more accurate description of the molecular mass distribution of a polymer than an "average molecular weight" value. The i.v. is measured as a function of volume per unit mass and is generally expressed in decilitres per gram (dl/g).

In one aspect of the invention there is provided a polymer microparticle, of size up to 10 microns in diameter, and containing a bioactive agent, wherein the polymer is PLG of inherent viscosity less than 0.5 dl/g. The bioactive agents can be DNA, such as DNA encoding a polypeptide than is expressed following administration to a recipient or encoding an antisense sequence.

This confers the advantage that the microparticle can be broken down once inside a recipient and having been taken up by antigen presenting cells but before a significant proportion of the DNA has degraded.

It is preferable to obtain a release profile where the maximum amount of encapsulated DNA is released when the majority of the microparticles have been taken up and internalised by cells. Typical release profiles of preferred embodiments of the invention provide for 30 to 40% release of the encapsulated DNA between 1 and 20 days, more preferably between 2 and 10 days, following administration to an animal. When administration is via the oral route it is preferred that significant DNA release occurs after passage of the microparticles through the stomach and into the gut of the animal where the microparticles are then taken up by the M cells of the Peyer's patches where they then degrade and release the encapsulated DNA.

It has been discussed above how using PLG of low i.v. (typically low molecular weight) might give improved immunisation, due to more rapid breakdown of particles and release of particle contents than using the standard 60 kD PLG (having high i.v.). Nevertheless, if a composition comprising microparticles having a range of i.v.s (and hence a range of molecular weights) is used, it can be an advantage that this combination produces an advantageous immunisation effect.

In a specific embodiment of the present invention release profiles for the microparticles can be engineered by adjusting the i.v. and/or molecular mass distribution of the polymer. In a specific example of the invention described in more detail below, this adjustment is made by combining PLG preparations of higher and lower i.v. values to produce a composite polymer of intermediate i.v. The microparticles made with intermediate i.v. PLG exhibit a modified DNA release profile wherein the greater the proportion of the lower i.v. polymer present the more quickly the DNA is released. In this way microparticles of the invention are produced that exhibit the desired release profiles suitable for oral and other administration routes.

Preferably, the i.v. is in the range of 0.1 to 0.4 dl/g. In specific embodiments of the invention it has been found that microparticles with polymer shells made of PLG having an i.v. within this range have exhibited good DNA release profiles and retained good particulate structure when examined under the scanning electron microscope. In particular examples of the invention described below, particles have been made with mixtures of PLG having i.v. of 0.19 dl/g and 0.39 dl/g and these particles showed very good release profiles over time.

The present invention relates also to vaccination therapies and methods using the microparticles of the present invention. Accordingly, the present invention further provides a method of making a microparticle for use as or in a vaccinating composition, comprising following the methods of the present invention, wherein the microparticle contains DNA coding for an antigen.

Still further the present invention provides a composition for use as or in a vaccinating composition, comprising a composition of the invention as previously recited wherein the microparticle contains DNA coding for an antigen, and use of a composition according to the invention in manufacture of a medicament for vaccination, wherein the microparticle contains DNA coding for an immunogen.

In a specific embodiment of the present invention, the microparticles are located within or are surrounded by a matrix. Such a matrix is made preferably from biodegradable material that breaks down over time to release microparticles either in a steady stream or in periodic pulses. The depot of the invention is typically administered subcutaneously or implanted into another part of the body. It is preferable that the depot be partly resistant to rehydration so that the particles located within the core remain in a dehydrated state until they are released, thereby ensuring that the encapsulated DNA is of high integrity for substantially the full lifetime of the depot. Examples of materials suitable for manufacture of such depots are commonly known to the art and include but are not limited to, polyhydroxybutyric acid; polycaprolactone; silicone; ethylene vinyl acetate and polyvinyl acetate.

Following the methods of preferred embodiments of the invention, the majority (typically 90% or more) of microparticles obtained lie in the size range of 10 or less micrometres. Electron micrographs of microparticle preparations show the majority of these seem to be shells (FIG. 3b). The presence of smaller microparticles is not detrimental to the efficacy of the preparation as microparticles smaller than 1 micrometres are still known to be actively phagocytosed by M cells and subsequently transferred to cells of the gut associated lymphoid tissue (GALT). Indeed, small (less than 2 microns diameter) sized microparticles have been suggested as being advantageous in promoting uptake by phagocytic cell and M-cells of the gut. The major barrier to preparing small particles containing active bio-active molecules has been the need to introduce large amounts of potentially damaging energy in order to prepare the desired size distribution. A clear advantage of the current invention is that the additional control of energy input using the blender technology will allow the generation of smaller particles without denaturation of the bio-active molecule. It also offers the possibility of large-scale production of these potentially improved delivery vehicles.

Size of microparticles is very important in the process of phagocytosis of microparticles by M cells and for cell to cell transfer. It is known that microparticles of sizes greater that 10 microns are not taken up and transported across the gut epithelium. In some of the preparations made according to the prior art we have seen significant numbers of microparticles with diameters 10 to 60 microns, ie larger that the optimum size required. If it is considered that the volume of a sphere is calculated on a cube function, it is entirely feasible that in such preparations most of the pDNA, could be contained inside the large shells. This would make it unavailable to the immune system and thus the dose could be considerably lower than anticipated, a problem overcome herein as following the methods described in the present invention which results in microparticle preparations having a majority of microparticles in the desired size range of up to 10 microns.

Control of the release characteristics of the microparticles of the invention has been addressed. Exactly how the bioactive agent is released from the micro-shell is unclear—possibly as a burst once the shell degrades by hydrolysis. This results in a sustained release as microparticle disruption occurs at different times. The time range may conceivably be over a shorter period than previously contemplated and is controllable through polymer molecular weight as described.

A range of surfactants are suitable for use in the method of the invention, and the present invention is not limited to the particular surfactant used in the examples, polyvinylalcohol. Other acceptable surfactants are known in the art, and methyl cellulose is a further example. The surfactant has the role of stabilising the double emulsion. Choice of aqueous surfactant is a matter for the skilled person and this choice may be made with regard to the choice of polymer and polymer solvent.

Other relevant background to the uptake of microparticles by M cells in the gut is provided in:

Jepson M A et al, Journal of Drug Targeting, 1993, Vol. 1, pp 245–249;

Howard K A et al, Pharmaceutical Science Communications, 1994, Vol. 4, pp 207–216;

Neutra M R et al, Cell, 1996, Vol. 86, pp 345–348;

Florence A T, Pharmaceutical Research, 1997. Vol. 14, pp 259 et seq;

O'Hagan D T, J. Anat., 1996, Vol. 189, pp 477–482; and

Kreuter J, J. Anat., 1996, Vol. 189, pp 503–505.

The following examples are illustrative, but not limiting, of the method and compositions of the present invention. Other suitable modifications and adaptations of the variety of conditions and parameters normally encountered and which are obvious to those skilled in the art are within the spirit and scope of the invention.

EXAMPLE 1

Microencapsulation Standard Method

Microparticles were prepared following the method now set out, which method is referred to as the microencapsulation standard method.

1. A 10% (w/v) 50:50 low iv (60kD) PLG solution in ethyl acetate (dried over sodium carbonate) is prepared by heating the mixture to around 37 degrees C and rolling until dissolution is complete.

2. A plasmid DNA solution is prepared to a concentration of 10 mg/ml in STE buffer (10 mM Tris HCl, pH 8.0; 1 mM EDTA;150 mM NaCl).

3. The PLG ethyl acetate solution (4 ml) is homogenised at 3000 rpm using a Silverson homogeniser and the plasmid DNA (600 microlitres) added. The resultant mixture is homogenised for a further 2.5 minutes.

4. An 8% (w/v) aqueous polyvinyl alcohol solution (92 ml) is homogenised in a round bottom flask at around 3000 rpm the first emulsion is added and the resultant mixture homogenised for a further 2.5 minutes.

5. The emulsion is poured into doubly distilled water (100 ml-1 L) at 37 degrees C and stirred for at least 20 minutes.

6. The microparticles are recovered by centrifuging at 10,000 rpm for 25 minutes at 25 degrees C.

7. The microparticles are washed by resuspending in doubly distilled water and centrifuging. This wash step is repeated such that a total of 5 spins are performed, to facilitate removal of the solvent and the emulsion stabilizer.

8. Following the 5th spin the pelleted microparticles are recovered as a slurry in a minimal quantity of doubly distilled water and freeze dried. A typical preparation is shown in FIG. 3a.

Variations to the Standard Method

Based on the above standard method a number of variations were made to the steps and/or the components, with results as follows:

1. Solutions of both 50:50 low (50 kD and below) MW and 50:50 high (70 kD and above) MW PLG in ethyl acetate have been studied and found to produce microparticle preparations of size up to 10 microns. Other PLG compositions e.g. 75:25 and polymers with higher or lower MW are also suitable for the microparticles and methods of the invention.

2. The w/v ratio of PLG to EA has been studied. With the high MW. polymer a reduction to 0.04 giml led to a marked decrease in incorporation efficiency (FIG. 1). The maximum amount tested was 0.125 g/ml, which improved encapsulation, produced microparticles in the size range 1 to 10 microns, but resulted in turbid solutions prior to encapsulation.

3. The use of co-solvents to increase the concentration of PLG in the organic phase has been studied. Co-solvents such as propylene carbonate and acetone in combination with ethyl acetate have enabled preparation of an initial water-in-oil emulsion having an increased amount of polymer dissolved in the oil (solvent) phase. This advantageously has been found to improve efficiency of incorporation of DNA into microparticles.

4. The ratio of aqueous phase to polymer phase in the first emulsification step has been varied within the ranges specified, and it is found that honey-comb structures are avoided and microparticle size can be controlled giving preparation of particles substantially all within the desired range and with the desired structures.

5. Homogenisation speed for first emulsification has been varied. Using a Silverson mixer, it is possible to increase the homogenisation speed to 4000 rpm while still retaining some DNA viability. However, 2000 rpm gives good DNA viability and is sufficiently non-damaging for extended homogenisation at this speed not to lead to significant DNA damage whilst allowing formation of microparticles having a narrow size distribution. 3000 rpm can also be used for extended time periods without significant DNA damage.

6. The concentration of PVA used is thought to be in excess and concentrations of 2% have been suggested as adequate. This will also have an effect on the viscosity of the mixture which may also affect microparticle stability and size.

7. The lowest volume of water successfully used in the final stage has been 150 ml. The stirring has been carried out at room temperature using water initially at 37 degrees C, and stirring has been continued for times from 20 minutes up to 1.5 hours, though there seems to be no theoretical upper limit to the stirring time.

8. The temperature at which the procedure is carried out will effect parameters such as the viscosity of the solutions and solubility of reagents in other phases. A single experiment carried out at 4 degrees C with ethyl acetate resulted in lower incorporation.

EXAMPLE 2

Comparison of Solvents and High and Low Molecular Weight 50:50 PLG

The following experiments were carried out using the standard method, in which EA=ethyl acetate and DCM=dichloromethane. The PLG volume in each case was 4 ml. No EtOH was used in any of the experiments. The results are shown in Table 1.

TABLE 1

| PLG M. Wt. | Concentration (%) | Solvent | Incorporation (ug/mg) | Efficiency (%) |
| --- | --- | --- | --- | --- |
| 60 kD | 12.5 | DCM | 1.4 | 8.9 |
| 90 kD | 10.0 | DCM | 1.4 | 6.6 |
| 60 kD | 12.5 | EA | 18.3 | 74.3 |
| 90 kD | 10.0 | EA | 11.8 | 62.8 |

EXAMPLE 3

Physical State of DNA Recovered from the Microparticles

FIG. 1—shows the physical state of the DNA recovered from microparticles prepared with dichloromethane and ethyl acetate. The lowest band is supercoiled DNA. The greater the intensity of this band the more the integrity of the DNA has been retained.

EXAMPLE 4

Transfection Results

Experiments were carried out with Vero cells. DNA was recovered from microparticles and Vero cells transfected using SUPERFECT REAGENT (Registered Trade Mark).

Further experiments were carried out transfecting vero cells with microparticles containing DNA but using no additional reagents to enhance transfection. The extent of transfection was assessed using a commercially available luciferase assay system and the results are shown in Table 2.

TABLE 2

| Sample | Reading |
| --- | --- |
| Negative control (cells only) | 9 |
| Positive control (2 ug pLuc) | 100000 (diluted 1:100) |
| DNA recovered from EA mps (2 ug pLuc) | 40748 (diluted 1:100) |
| pLuc containing mps prepared with EA | 29937 |

EXAMPLE 5

Effect of PLG Concentration

Table 3 below shows the results obtained when the concentration of low mol.wt (60kD) PLG was reduced. In these comparative experiments ethyl acetate was used as solvent, the volume of the organic phase was kept at 4 ml. Homogenisation speeds of 3000 rpm were used in all cases.

TABLE 3

| PLG Concentration (%) | Incorporation (ug/mg) | Efficiency (%) |
| --- | --- | --- |
| 10.0 | 18.3 | 74.3 |
| 8.0 | 12.4 | 51.1 |
| 6.0 | 12.3 | 39.1 |

EXAMPLE 6

Use of Co-solvents

High molecular weight PLG is not totally soluble at or above 10% w/v in ethyl acetate. In order to increase the PLG concentration the application of mixtures of solvents such as ethyl acetate and propylene carbonate was investigated.

80% ethyl acetate: 20% propylene carbonate gives a clear solution of 10%w/v PLG.

EXAMPLE 7

Release kinetics

Samples of microparticles prepared with ethyl acetate using high and low MW polymers were studied to determine the release characteristics. The microparticles were added to sterile STE buffer and maintained at 37 degrees C with an appropriate antibacterial agent. Samples were removed at intervals and the DNA released and retained determined. From this data percentage release with time profiles were determined. The results are shown below in FIG. 2.

EXAMPLE 8

Microparticles Prepared Using Polycaprolactone as the Polymer

Microparticles are prepared using polycaprolactone polymer by the following method 1. A 100 mg/ml solution of polycaprolactone (average MW =14 kD; Aldrich Chemical Company) in ethyl acetate is prepared by vortexing until dissolution is complete.

2. A plasmid DNA solution is prepared to a concentration of 9.9 mg/ml in STE buffer (10 mM Tris HCl, pH 8.0; 1 mM EDTA; 100 mM NaCl).

3. The polycaprolactone ethyl acetate solution (4 ml) is homogenised at low power in a Waring blender and the plasmid DNA (400 microlitres) added. The resultant mixture is homogenised for four fifteen second cycles intercalated with 15 second rest periods.

4. An 8% (w/v) aqueous polyvinyl alcohol solution (66 ml) is homogenised in a Waring blender at low power, the first emulsion is added and the resultant mixture homogenised for four fifteen second cycles intercalated with 15 second rest periods.

5. The emulsion is poured into doubly distilled water (300 ml) at 37 degrees C and stirred for at least 20 minutes.

6. The microparticles are recovered by centrifuging at 10,000 rpm for 25 minutes at 25 degrees C.

7. The microparticles are washed by resuspending in doubly distilled water and centrifuging. This wash step is repeated such that a total of 5 spins are performed, to facilitate removal of the solvent and the emulsion stabilizer.

8. Following the 5th spin the pelleted microparticles are recovered as a slurry in a minimal quantity of doubly distilled water. Microparticles are obtained predominantly in the size range 1–10 microns in diameter and are then freeze dried for storage.

EXAMPLE 9

Modification of Release Profiles of PLG Microparticles by Altering the Inherent Viscosity of the Polymer The procedure of Example 8 was followed using the following PLG preparations:

(a) inherent viscosity of 0.19 dl/g (RG502, from Boehringer Ingelheim)

(b) inherent viscosity of 0.39 dl/g (RG503, from Boehringer Ingelheim)

(c) mixture of 50:50 by weight of PLG of inherent viscosities 0.19 and 0.39 dl/g (mixture of RG502 and RG503).

(d) mixture of 75:25 by weight of PLG of inherent viscosities 0.19 and 0.39 dl/g (mixture of RG502 and RG503).

Microparticles of size predominantly 1 to 10 microns are obtained and the profiles of release of DNA from the particles measured and illustrated in FIG. 5.

EXAMPLE 10

The protocol of Example 8 was followed with the following variations: 8 ml of polymer solution and 0.8 ml of plasmid solution were used and 132 ml PVA was used to stabilize the first emulsion.

Plasmids were encapsulated in PLG as follows:

(a) mixture of 50:50 RG502: RG503;

(b) the (a) mixture repeated;

(c) mixture of 70:30 RG502: RG503;

(d) the (c) mixture repeated.

Microparticles of size predominantly 1 to 10 microns diameter were obtained and tested for efficiency of DNA incorporation. From the microparticles of (a) and (b) 65% was recovered as encapsulated DNA and from those of (c) and (d) 69%. This % figure does not make allowance for the fact that a proportion of the DNA is lost in isolation of the particles, for example by centrifugation, and that as a consequence recovery can not be 100% efficient. The figures achieved in these examples thus represent very high efficiency of incorporation.

The invention thus provides further and improved methods of encapsulation of bioactive agents, DNA in particular, and further an improved compositions comprising microparticles containing bioactive agents, for gene therapy and/or vaccination and other applications.

TABLE 4

ACCESSION NUMBERS OF GENE SEQUENCES IDENTIFIED AS PUTATIVE OR PROTECTIVE ANTIGENS AGAINST SPECIFIC PATHOGENS

| Organism | Protein/Glycoprotein | Accession Number | Database |
|---|---|---|---|
| *Bordetella Pertussis* | FHA; PT | P12255; M13223 | Swiss Prot; Genbank |
| *Bordetella Bronchiseptica* | 68 kD-Pertactin | X54815 | Genbank |
| *Clostridium Tetani* | Tetanus Toxin | P04958 | Genbank |
| CMV | gp48 | A32390 | Swiss Prot |
| Dengue Virus | NS1; Capsid | S37468; Z794047 | Swiss Prot |
| EBV | gp350 | A43042; S33008; A03762 | Swiss Prot |
| Flavivirus | NS3 | S79821; S79825; S79826; S79830 | |
| Hepatitis B Virus | SA | V00867; X02763 | Genbank |
| Herpes Simplex Virus | I | P06487 | Genbank |
| Influenza Virus | NP | H36754 | Swiss Prot |
| JEV | E; M; gp340 | M18370 | Swiss Prot |
| Measles Virus | F; H | D00090; N00090; Z80790 | Genbank |
| Mumps Virus | HN | X93178 | Genbank |
| Mycobacteria Tuberculosis | 35 kD protein | M69187 | Genbank |
| Rotavirus | VP1 | P35942 | Swiss Prot |
| Rubella Virus | E1; E2 | A27505; D00156 | Swiss Prot, Genbank |
| TBE | C; M; E | X07755; M97369 | Genbank |
| *Vibrio Cholerae* | MSHA | X77217 | Genbank |

All publications, patents and patent applications mentioned in this specification are indicative of the level of skill of those in the art to which the invention pertains. All publications, patents and patent applications are herein incorporated by reference to the same extent as if each individual publication or patent application was specifically and individually indicated to be incorporated by reference in their entirety.

What is claimed is:

1. A method for encapsulating DNA in a polymer microparticle, comprising:
    dissolving polymer in a solvent to form a polymer solution;
    preparing an aqueous solution of DNA;
    combining the polymer and aqueous solutions with agitation to form a water-in-oil emulsion;
    adding the water-in-oil emulsion to a further aqueous phase with agitation to form a (water-in-oil)-in-water emulsion;
    adding the (water-in-oil)-in-water emulsion to excess of an aqueous phase to extract the solvent, thereby forming polymer microparticles of a size up to 10 microns in diameter, said microparticles containing DNA in aqueous solution;
    wherein the solvent comprises ethyl acetate.

2. A method according to claim 1, wherein the ratio of solvent:aqueous phase in formation of the water-in-oil emulsion is in the range of 4:1 to 20:1 (volume:volume).

3. A method for encapsulating a bioactive agent in a polymer microparticle, comprising:
    dissolving polymer in a solvent to form a polymer solution;
    preparing an aqueous solution of a bioactive agent;
    combining the polymer and aqueous solutions with agitation to form a water-in-oil emulsion;
    adding the water-in-oil emulsion to a further aqueous phase with agitation to form a (water-in-oil)-in-water emulsion;
    adding the (water-in-oil)-in-water emulsion to excess of an aqueous phase to extract the solvent, thereby forming polymer microparticles of a size up to 10 microns in diameter said microparticles containing bioactive agent in aqueous solution;
    wherein the solvent comprises ethyl acetate, wherein the ratio of solvent:aqueous phase in formation of the water-in-oil emulsion is in the range of 5:1 to 12:1 (volume:volume).

4. A method according to claim 1 wherein the polymer is PLG and the solvent comprises a mixture of ethyl acetate and a co-solvent which increases the amount of PLG that can be dissolved in the solvent provided that the major proportion of the mixture is ethyl acetate.

5. A method according to claim 1 comprising maintaining the agitation of the polymer and aqueous solutions to form the water-in-oil emulsion over a prolonged period of time so as to obtain microparticles the majority of which are of a size up to 10 microns in diameter.

6. A method according to claim 1 comprising maintaining the agitation of the polymer and aqueous solutions to form the water-in-oil emulsion over a prolonged period of time so as to obtain microparticles the majority of which are of a size up to 10 microns in diameter and more than 1 micron in diameter.

7. A method for encapsulating DNA in a polymer microparticle, comprising:
    dissolving polymer in a solvent to form a polymer solution;
    preparing an aqueous solution of DNA;
    combining the polymer and DNA solutions with agitation to form a water-in-oil emulsion;
    adding the water-in-oil emulsion to a further aqueous phase with agitation to form a (water-in-oil)-in-water emulsion;
    adding the (water-in-oil)-in-water emulsion to excess of an aqueous phase to extract the solvent, thereby forming polymer microparticles of a size up to 10 microns in diameter, said microparticles containing DNA in aqueous solution;
    wherein the DNA comprises a coding sequence that is expressed in a recipient following oral administration, and wherein the solvent comprises ethyl acetate.

8. A method of making a microparticle for use as or in a vaccinating composition, comprising following the method according to claim 7 wherein the microparticle contains DNA coding for an antigen.

9. A method for encapsulating a bioactive agent in a polymer microparticle, comprising:

dissolving polymer in a solvent to form a polymer solution;

preparing an aqueous solution of a bioactive agent;

combining the polymer and aqueous solutions with agitation to form a water-in-oil emulsion;

adding the water-in-oil emulsion to a further aqueous phase with agitation to form a (water-in-oil)-in-water emulsion;

adding the (water-in-oil)-in-water emulsion to excess of an aqueous phase to extract the solvent, thereby forming microparticles of a size up to 10 microns in diameter, said microparticles containing bioactive agent in aqueous solution;

wherein the agitation steps comprise agitating the solutions or emulsions in the blending compartment of a blender, and using a blending blade which both blends and mixes the contents of the blending compartment.

10. A method according to claim 9 wherein the blending is continued for a prolonged period of time so as to obtain microparticles the majority of which are of a size up to 10 microns in diameter.

11. The method of claim 4, wherein the co-solvent comprises propylene carbonate.

12. The method of claim 4, wherein the co-solvent comprises acetone.

13. A method according to claim 7 wherein the polymer is PLG and the solvent comprises a mixture of ethyl acetate and a co-solvent which increases the amount of PLG that can be dissolved in the solvent, provided that the major proportion of the mixture is ethyl acetate.

14. A method according to claim 7 comprising maintaining the agitation of the polymer and aqueous solutions to form the water-in-oil emulsion over a prolonged period of time so as to obtain microparticles the majority of which are of a size up to 10 microns in diameter.

15. A method according to claim 7 comprising maintaining the agitation of the polymer and,aqueous solutions to form the water-in-oil emulsion over a prolonged period of time so as to obtain microparticles the majority of which are of a size up to 10 microns in diameter and more than 1 micron in diameter.

* * * * *